US00PP09916P

United States Patent [19]

Gargiulo

[11] Patent Number: Plant 9,916

[45] Date of Patent: Jun. 10, 1997

[54] '552' GRAPEVINE

[75] Inventor: Angel A. Gargiulo, Mendoza, Argentina

[73] Assignee: Luis M. Caratan, Delano, Calif.

[21] Appl. No.: 517,779

[22] Filed: Aug. 22, 1995

[51] Int. Cl.[6] ..... A01H 5/00

[52] U.S. Cl. ..... Plt./47.1

[58] Field of Search ..... Plt./47.1

*Primary Examiner*—James R. Feyrer

*Attorney, Agent, or Firm*—Worrel & Worrel

[57] ABSTRACT

A new and distinct variety of grapevine which is somewhat remotely similar to the "Flame Seedless" grapevine (Unpatented), but from which it is distinguished by producing fruit which are mature for harvesting and shipment approximately August 1, or about two weeks after the fruit produced by the "Flame Seedless" grapevine, and wherein the fruit is of high quality and of dark maroon red to lighter red skin coloration.

1 Drawing Sheet

BACKGROUND OF THE NEW VARIETY

The present invention relates to a new and distinct variety of grapevine, which will hereinafter be denominated varietally as the "552" grapevine, and, more particularly, to a grapevine which produces seedless fruit, which are mature for commercial harvesting and shipment approximately August 1 to August 20 in the San Joaquin Valley of central California.

The "Flame Seedless" grapevine has been a very successful commercial variety for numerous reasons. Principally, the "Flame Seedless" grapevine produces high quality and high colored fruit which are ripe for commercial harvesting and shipment in the San Joaquin Valley of California in approximately mid July. The red skin coloration and excellent flavor causes the fruit to have a virtually universal appeal.

Where a variety excels in the marketplace, it has long been recognized that there is a commercial advantage in the development of varieties having closely similar characteristics which are available for market immediately after the end of the season for the existing commercially successful variety. This, in effect, extends the commercial season by continuing to be able to fill the market demand and retain commercial interest in the marketplace. While the desirability for finding such a new variety relative to the "Flame Seedless" grapevine has been recognized, no such new variety has previously been discovered which was entirely successful. The variety of the instant invention appears to be a promising candidate to fill this void.

ORIGIN AND ASEXUAL REPRODUCTION OF THE NEW VARIETY

The present variety of grapevine hereof was bred by the inventor, through cross pollination, in San Rafael, Province of Mendoza, Argentina, in 1987. The parent varieties of the new variety of the present invention are the "Patagonia" grapevine, a seeded grapevine, and the "Galaxy" grapevine, a seedless grapevine. Seeds were brought to California and planted in a vineyard near Delano in the San Joaquin Valley of central California in 1988. The new variety of grapevine was first asexually reproduced in the United States in the spring of 1992 by grafting scions of the new variety onto one year old "Salt Creek" grapevine rootstock. The grapevines of the new variety produced their first crop in the United States in 1993.

SUMMARY OF THE NEW VARIETY

The new grapevine of the subject invention, of the *Vitis vinifara* genus and species, is characterized by producing high quality, well colored, red skinned table grapes which ripen for commercial harvesting and shipment approximately two weeks after the "Flame Seedless" grapevine approximately August 1 to August 20 in the San Joaquin Valley of central California. The bunch counts of the new variety are somewhat less than those of the "Flame Seedless" grapevine, but the larger berry size of the subject variety tend to produce approximately the same tonnage per acre. Furthermore, the coloration of the berries of the new variety develops exceedingly well in contrast with those of the "Flame Seedless" grapevine which require significant leaf removal for coloration fully to develop.

BRIEF DESCRIPTION OF THE DRAWING

The accompanying drawing is a color photograph of representative portions of the new grapevine of the present invention including bunches of grapes and sectioned portions of individual berries thereof and typical foliage and segments of canes of the new variety.

DETAILED DESCRIPTION

Referring more specifically to the viticultural details of this new and distinct variety of grapevine, the following has been observed under the ecological conditions prevailing at the vineyard of origin which is located near Delano in the San Joaquin Valley of central California. All major color code designations are by reference to the *Dictionary of Color*, by Maerz and Paul, First Edition, 1930. Common color names are also occasionally employed.

VINE

Generally:

*Size.*—Medium. The new variety is slightly larger than the "Flame Seedless" grapevine and about equal to the "Thompson Seedless" grapevine. Vines of the subject variety are planted eight feet apart in the test rows and essentially extend a full four feet on either side of the individual trunks. Individual vines extend from 5.5 feet (167.64 cm) to 6.5 feet (198.12 cm) in width perpendicular to the row.

*Vigor.*—Vigorous in growth characteristic, about equal to the "Flame Seedless" grapevine.

*Figure.*—Cane pruned.

*Productivity.*—Moderately productive. Fewer bunches are present than on the "Flame Seedless" grapevine, although larger berry size potential tends to equalize the eventual tonnage on a per acre basis. The test vines have been trained to a cane system in order to maximize bunch counts. Vines in the test planting had been girdled in 1993 and had received one application of gibberellic acid for fruit sizing, but had not received a second application for berry thinning.

*Regularity of bearing.*—Crop yields are consistent from year to year.

Trunk:

*Size.*—Medium. Ranges from 38 mm (1.52 inches) to 55 mm (2.2 inches).

*Surface texture.*—Rough with a fibrous, shaggy exterior.

*Color.*—Light maple brown (14-G-9).

Canes:

*Size.*—Thickness — Medium. Ranges from 9 mm (0.36 inches) to 15 mm (0.6 inches) in diameter for the largest canes.

*Surface texture.*—The mature cane surface is usually relatively smooth, occasionally with slight ribbing.

*Form.*—Woody shoot cross sectional form is variable, from perfectly circular to slightly elliptic.

*Color.*—One year or older — Light hazel brown (13-I-9) overlain with frequent longitudinal striping of a darker chestnut brown, Piccadilly Brown (7-H-10).

*Internode.*—Length — Average to slightly less than average with a joint frequency of 60 mm (2.4 inches) to 114 mm (4.56 inches).

Tendrils:

*Size.*—Length — Slender and moderately long, from 15.5 cm (6.045 inches) to 25.4 cm (9.906 inches on well developed canes.

*Distribution.*—Discontinuous.

*Form.*—Predominantly trifid, although bifid tendrils can frequently be present.

*Color.*—Pale green (13-L-1) to a bronze green (13-L-5) with at times a very slight rust red tinge.

Growing tips: Tip inducement is slightly pubescent with relatively short pubescence.

*Color.*—Leaves on the expanding growing tip are a bronze (13-L-6) to bronze rust color (13-L-8) with only slight anthocyanin intensity.

LEAVES

Size:

*Generally.*—Five lobed with broadly serrated margins.

*Average leaf blade length.*—Large mature leaves ranges from 119 mm (4.76 inches) to 147 mm (5.88 inches) when measured from the petiolar junction to the apex of the center lobe.

Color:

*Upwardly disposed surface.*—Dark green (24-E-8) with usually no red anthocyanin color development on the primary veins.

*Downwardly disposed surface.*—Lighter green Peridot green (22-L-6).

*Leaf vein.*—Pale green (17-F-4) occasionally with very light anthocyanin pigmentation.

Marginal form:

*Generally.*—Broadly serrate.

Petiolar sinus:

*Form.*—Distinctly "U" shaped and quite open. The upper leaf sinuses are closed, with the lobes usually distinctly overlapping. The base of the upper leaf sinuses are usually "U" shaped and are often toothed basally, especially on the largest and most mature leaves.

Lobe apices:

*Form.*—Acute.

Leaf vein:

*Thickness.*—Average.

Leaf margin: The mature leaves are generally pentagonal with a relatively smooth surface. Straight with only occasionally slightly convex sides.

*Length.*—Relatively long with the largest teeth. Ranges from 2 mm (0.08 inches) to 5 mm (0.2 inches).

Petiole:

*Size.*—Medium to slightly less than medium.

*Length.*—Within the medium range, from 98 mm (3.92 inches) to 109 mm 4.36 inches).

*Thickness.*—Mid petiole varies from 2.5 mm (0.1 inches) to 3.0 mm (0.12 inches).

*Color.*—Light green (19-J-3), slightly darker basally and with rose Roseglow (5-D-9) to red anthocyanin Rose of Sharon (3-K-8) pigmentation at times present. Reddish pigmentation is usually more evident near the petiolar junction with the base of the leaf blade.

Stipules: None present.

FLORAL

Cluster:

*Generally.*—The floral cluster is moderately narrow and tapering. The first floral cluster occurs from the fourth to the sixth joint, most frequently on joint 4 or 5. The cluster frequency is less than average.

*Size.*—Length — At bloom ranges from 28 mm (1.12 inches) to 49 mm (1.96 inches) from the base of the peduncle to the tendril and from 25 1 mm (1 inch) to 32 mm (1.28 inches) from the tendril to the first rachis branch.

*Total floral cluster — size — length.*—Ranges from 15.0 cm (5.85 inches) to 19.5 cm (7.605 inches) minus the peduncle.

*Total floral cluster — size — width.*—Ranges from 5.0 cm (1.95 inches) to 9.0 cm (3.51 inches).

*Flowers.*—Hermaphroditic with medium length.

*Stamens.*—Upright.

*Anthers.*—Size — Average.

*Date of bloom.*—Full bloom occurred on May 7, 1994 near Delano, Calif. In 1994 this bloom timing occurred approximately one day ahead of the "Thompson Seedless" grapevine, and approximately four days after the "Flame Seedless" grapevine. Length of blooming season is approximately ten days.

*Pollen.*—Abundant.

*Calyptra.*—Separates completely from the flower base.

*Petiole — color.*—Light green (20-J-4) to Verdant green (20-K-5) at bloom.

*Calyptra — color.*—Medium green, Lettuce green (20-L-5).

FRUIT

Maturity when described: Ripe for commercial harvesting and shipment Aug. 1, 1993 to Aug. 20, 1993 near Delano, Calif.

Cluster:

*Generally.*—Fruit cluster medium to large.

*Bunch — length.*—Ranges from 20.8 cm (8.112 inches) to 25.8 cm (10.062 inches).

*Bunch — width.*—Ranges from 12.2 cm (4.758 inches) to 17.6 cm (6.864 inches).

*Bunch — density.*—Loose with a moderate number of pedicels visible.

*Berry — number.*—Slightly less than average and ranges from 86 to 106 in count within the largest bunches.

*Bunch — peduncle — length.*—Varies from 37 mm (1.48 inches) to 54 mm (2.16 inches).

*Bunch — peduncle — thickness.*—Ranges from 3.5 mm (0.14 inches) to 5.5 mm (0.22 inches).

*Peduncle — color.*—Medium green, Biscay Green (21-K-5).

Berry:

*Shape.*—Strongly obovate in lateral aspect with large bell-shaped berries. Berry cross section is slightly variable from globose to slightly elliptical.

*Uniformity.*—Within the bunch is very good.

*Size — diameter.*—Ranges from 22 mm (0.88 inches) to 25 mm (1 inch).

*Size — length.*—25 mm (1 inch) to 28 mm (1.12 inches).

*Berry color — generally.*—Only slightly variable and moderately dependent on bunch exposure.

*Skin — color — generally.*—Quite uniform. The berry is usually covered with a light, uniform, greyish colored bloom. The bunches color uniformly even under shaded canopies.

*Skin — color.*—The darkest color phase is a dark maroon-red, Tapestry Red (7-J-5) shading to a lighter red, Mineral Red (6-J-3). Usually the lighter coloration is at the base of the berry. Some interior berries on less exposed bunches at times have a pale greenish (13-K-1) hue basally near the pedicel.

*Pedicel — length.*—Medium. Ranges from 10 mm (0.4 inches) to 14.8 mm (0.592 inches).

*Pedicel — thickness.*—Ranges from 1.5 mm (0.06 inches) to 2.0 mm (0.08 inches) at mid pedicel.

*Pedicel — color.*—Green, Certosa green (20-L-3).

*Pedicel.*—Very attached to the berry. Almost no shatter occurs even at full maturity.

Flesh:

*Flesh color.*—Variable, from a medium pink rose (5-F-4) to lighter pink (3-G-7) Lilac. A light geenish (12-H-1) hue can be present near the center of the berry.

*Juice production.*—Juicy.

*Flavor.*—Sweet, mild with only moderate acidity. Very well balanced and pleasant.

*Aroma.*—Very slight, pleasant.

*Texture.*—Firm and crisp.

*Ripening.*—Uniform.

*Eating quality.*—High quality.

Seeds: Usually absent. Only occasionally can one or two small, undeveloped, rudimentary seed traces be found.

Use: Fresh table grape: A high quality, seedless, red-skinned grape suitable for fresh consumption.

Secondary bunches: The secondary bunches are few in number and small in size. Bunch form is irregular but berry shape and coloration is similar to that of the primary clusters. Secondary bunch width varies from 58 mm (2.32 inches) to 82 mm (3.28 inches). Secondary bunch length ranges from 45 mm (1.8 inches) to 79 mm (3.16 inches). Berry count of secondary bunches ranges widely from 6 to 23 berries.

Keeping quality: The stem retains turgidity for an extended period of time.

Resistance to disease: No unusual susceptibilities to disease have been noted.

Harvesting: Uniform.

Although the new variety of grapevine possesses the described characteristics noted above as a result of the growing conditions prevailing near Delano, Calif. in the central San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of grapevine, what I claim as new and desire to be secured by Plant Letters Patent is:

1. A new and distinct variety of grapevine substantially as illustrated and described which is somewhat remotely similar to the "Flame Seedless" grapevine (Unpatented), but from which it is distinguished by producing high quality seedless fruit having a red skin coloration which are mature for commercial harvesting and shipment approximately August 1, or about two weeks after the fruit of the "Flame Seedless" grapevine, in San Joaquin Valley of central California.

* * * * *

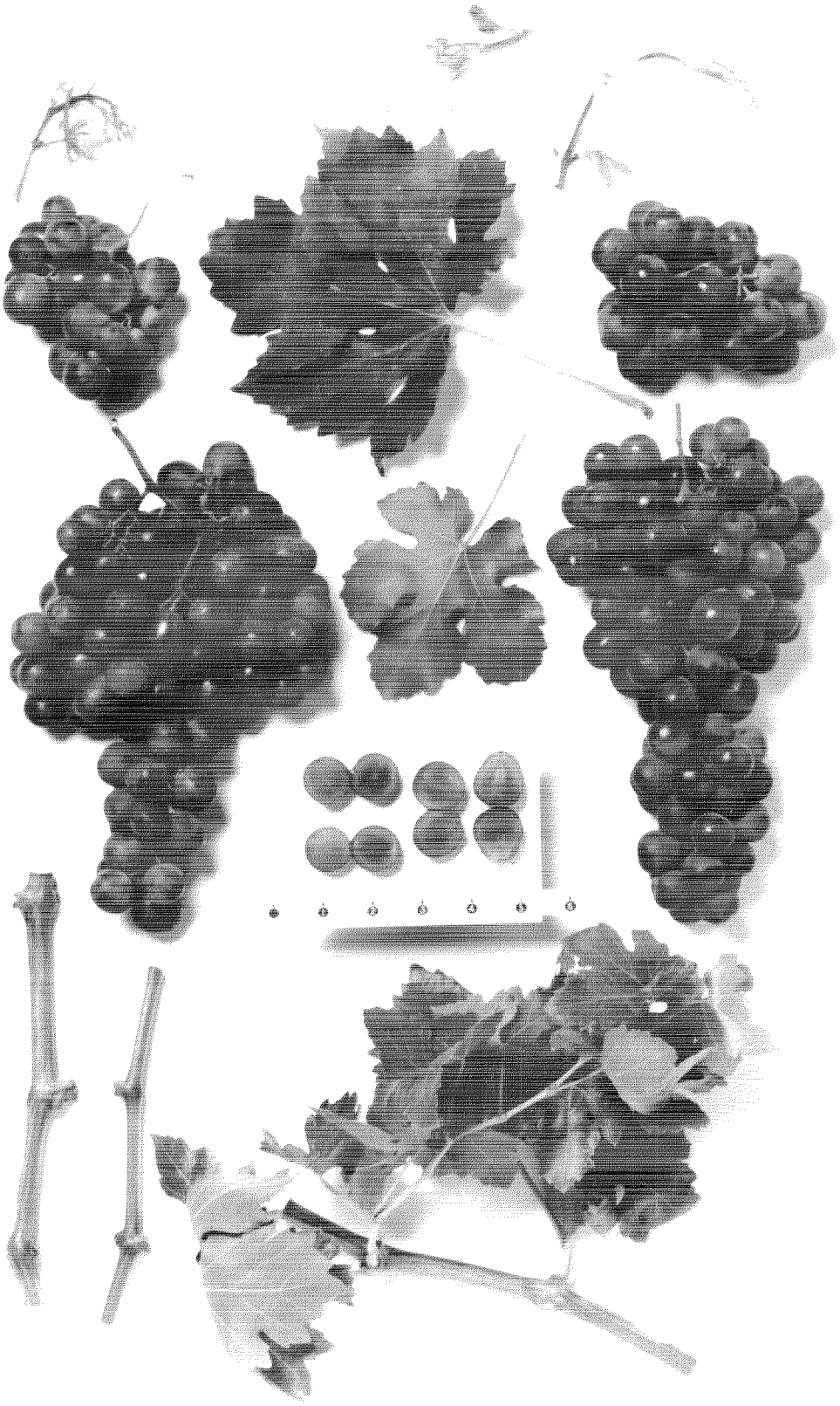

UNITED STATES PATENT AND TRADEMARK OFFICE

CERTIFICATE OF CORRECTION

PATENT NO. : Plant 9,916

DATED : June 10, 1997

INVENTOR(S) : Angel A. Gargiulo

It is certified that error appears in the above-identified patent and that said Letters Patent is hereby corrected as shown below:

Column 4, Line 40, delete "25 1 mm" and substitute ---25 mm---.

Signed and Sealed this

Nineteenth Day of August, 1997

*Attest:*

Bruce Lehman

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : PP 9,916

DATED : June 10, 1997

INVENTOR(S) : Angel A. Gargiulo

It is certified that error appears in the above-identified patent and that said Letters Patent is hereby corrected as shown below:

Column 5, Line 48, delete "geenish" and substitute ---greenish---.

Signed and Sealed this

Seventh Day of October, 1997

*Attest:*

*Attesting Officer*

BRUCE LEHMAN

*Commissioner of Patents and Trademarks*